United States Patent [19]

Fadulu

[11] Patent Number: 5,447,720
[45] Date of Patent: Sep. 5, 1995

[54] COMPOSITION AND METHOD FOR TREATMENT OF HEMOGLOBINOPATHIES

[75] Inventor: Sunday O. Fadulu, 20115 Wickham Ct., Katy, Tex. 77450

[73] Assignee: Sunday O. Fadulu, Katy, Tex.

[21] Appl. No.: 88,084

[22] Filed: Jul. 6, 1993

[51] Int. Cl.$^6$ ............................................. A61K 35/78
[52] U.S. Cl. ................... 424/195.1; 514/783; 514/815; 514/822; 514/834
[58] Field of Search .............. 424/195.1; 514/783, 514/815, 822, 834

[56] References Cited

U.S. PATENT DOCUMENTS 3,102,891  9/1963  Allen ................................. 260/314
4,473,559  9/1984  Robinson ........................ 424/195.1

OTHER PUBLICATIONS

Adekile, Adeodu, Fadulu, Weinhemer, and Sanduja, *Preliminary Clinical Trial of Nix-06999 in the Management of Sickle Cell Anemia*, vol. 20, No. 1, Nigerian Medical Journal (Jan.-Mar. 1990).

Adekile, Adeodu, and Fadulu, *Preliminary Clinical Trial of NX-06999 in the Management of Sickle Cell Anemia*, Dept. of Pediatrics and Chile Health, Faculty of Health Sciences, Obafemi Awolowo University, Ile-Ife, Nigeria, Dept. of Biology, Texas Southern University, Tex.

Fadulu, *Ethyl-Alcohol Extract from Fagara Zanthoxyloides Root: Invitro Effect on Red Blood Cells*, Faculty Research Journal, pp. 22-31, Texas Southern University.

Grant Application to the Department of Health and Human Services, Public Health Service, entitled "A New Drug for Sickle Cell Disease," Feb. 18, 1992.

Sofowora, Isaac-Sodeye, and Ogunkoya, *Isolation and Characteristics of an Antisickling Agent from Fagara zanthoxyloides Root*, vol. 38, No. 2, Lloydia, pp. 169-171 (Mar.-Apr. 1975).

Honig, Farnsworth, Ferenc, and Vida, *Evaluation of Fagara zanthoxyloides Root Extract in Sickle Cell Anemia Blood in Vitro*, vol. 38, No. 5, Lloydia, pp. 387-390 (Sep.-Oct. 1975).

Fadulu, *Translating African Medicine into Western Techno-scientific Concepts*, vol. 1, An International Journal of Traditional medicine, pp. 134-138 (1990).

Jones, Sandra Dianne, *The Effects of Fagara Zanthoxyloides (An Anti-Sickling Agent) on the Sickle Cell Membrane* (unpublished M.S. thesis, Texas Southern University (1979).

Somerville, Barry C., *Mechanism of an Antisickling Agent: Effect on the Concentration of 2, 3 DPG in Sickle Cell Anemia, Sickle Cell trait and Normal Hemoglobin* (unpublished M.S. thesis, Texas Southern University (1978).

Enigbokan, Mofolurunso A., *The Role of an Extract of Fagara Zanthoxyloides in the Inhibition of Dental Caries* (unpublished M.S. thesis, Texas Southern University) (1978).

Ekong, et al, *New Antisickling agent 3,4-dihydro-2,-2-dimethyl-2H-1 benzopyran-6-butyric acid*, vol. 258, Nature, pp. 743-746 (1975).

Primary Examiner—Douglas W. Robinson
Assistant Examiner—Howard C. Lee
Attorney, Agent, or Firm—James O. Okorafor

[57] ABSTRACT

A composition and method of treatment of hemoglobinopathies, such as, for example, sickle cell disease and thalassemia, wherein an inventive extract used in such treatment is obtained from alfalfa and other certain plant materials, preferably using a hydroxide base and hexane. In the most preferred embodiment, the plant material is first extracted with 1,1,1-trichloroethane and a hydroxide base, followed by extraction with hexane. The polar acidic compounds present in alfalfa and other plant materials selectively dissolve in the hexane phase and exhibit good antisickling activity in vitro. Further, these active compounds which comprise the inventive extract are effective in vivo by significantly alleviating the many clinical manifestations of sickle cell disease and thalassemia experienced by the affected patients.

6 Claims, 1 Drawing Sheet

COMPOSITION AND METHOD FOR TREATMENT OF HEMOGLOBINOPATHIES

BACKGROUND OF THE INVENTION

1. Field of the Invention

The present invention relates to the treatment of blood disorders; and in particular, to a method and composition for the treatment of hemoglobinopathies, including α-thalassemia, β-thalassemia, sickle cell diseases such as sickle cell SC (i.e., HbSC), sickle cell anemia (i.e., HbSS), and sickle cell trait (i.e., HbAS), for example, and combination hemoglobinopathies such as HbSS/β-thalassemia, for example.

Sickle cell disease is an inherited disease wherein the patient carries two abnormal $\beta^s$ genes, at least one of which codes for an abnormal type of hemoglobin molecule hemoglobin S (HbS). The disease itself stems from inadequate oxygen transport by red blood cells due to the presence of HbS. In sickle cell disease, HbS replaces normal hemoglobin, hemoglobin A (HbA), and differs from HbA only in that glutamic acid is substituted for valine at position 6 of the beta chain of the globin molecule. This one variation results in HbS being less soluble than HbA, especially in the reduced state, where it forms long, crystalline masses to cause the red blood cells to distort into the shape of sickles.

HbS is inherited as a mendelian dominant such that there are both homozygous and heterozygous states. The most common and most severe form of the disease is HbSS, the homozygous state, (also referred to as sickle cell anemia). HbSS makes up from 80% to 100% of the total hemoglobin in individuals affected with sickle cell disease. Sickle cell trait carriers (HbAS) are heterozygous for HbS and usually show no sign of the disease. However, since about 25% to 40% of the total hemoglobin in trait carriers is HbS, sickle cell trait carriers risk hemolysis when exposed to low oxygen tension, such as during anesthesia, for example. Statistically, the marriage of two trait carriers results in a 25% chance that one of their children will be afflicted with sickle cell disease (i.e., homozygous) and a 50% chance that their children will have the sickle cell trait (i.e., heterozygous). Other sickle hemoglobinopathies related to HbSS include HbSC, HbSD, and HbSE.

Sickle cell disease is most prevalent in the black races, but it is also known in other races surrounding the Mediterranean and in India. About 30% of Mediterranean people carry the trait (i.e., are carriers). About 1.2 million Afro-Americans carry the sickle cell trait while about another 0.2% have sickle cell disease. The disease, however, is much more prevalent in central Africa, where 40-45% carry the sickle cell trait, while about 4-10% have other hemoglobinopathies. For example, in Gabon, the disease represents 10-30% of out-patient pediatric consultations and 25% of in-patient pediatrics.

The most common manifestation of sickle cell disease, as well as other hemoglobinopathies, is an extremely painful "crisis," typically lasting several days, and affecting one or more local parts of the body. The crisis often occurs following physical stress, and appears to be due to limited oxygen supply to the affected part resulting from an inferior oxygen-carrying capability of HbS as well as to its tendency to aggregate in insoluble gels within the red blood cell to cause the cell to distort into the shape of a sickle. The sickling of the cells results in hemolytic anemia and capillary obstruction due to thrombosis. The resulting hypoxia leads to fatty degeneration in the liver, kidney, and heart. Other organs are also at risk to the effects of hypoxia due to vascular obstruction which may occur at many other sites in the body, as well.

The symptoms of sickle cell disease, usually related to the anemia, normally occur during the second year of life. Symptoms include slight jaundice, fever, and severe bone, joint, and abdominal pain. Children are particularly susceptible to infections such as salmonella osteomyelitis and bacterial meningitis. The prognosis for individuals with sickle cell disease is very poor, and those afflicted with severe forms of the disease usually do not live through their teen years.

Thalassemia is another inherited hemoglobinopathy in which there is a quantitative reduction in either the α-chains (α-thalassemia) or β-chains (β-thalassemia) of globin. In β-thalassemia, there is an increase in HbA$_2$ ($\alpha_2\delta_2$) and/or HbF ($\alpha_2\gamma_2$), due to the combination of α-chains, which are in excess, with δ and γ globin chains. In normal individuals, HbF is absent and HbA$_2$ comprises 2-4% of normal hemoglobin. About 30 million persons carry a β-thalassemia gene, and about 8,000-10,000 children are born with β-thalassemia major every year.

In thalassemia, the red blood cells are thinner and more fragile than normal red blood cells. Further, the excess α-chains present in β-thalassemia also may contribute to hemolysis due to their instability. Thus, the red blood cells in this anemic blood disorder are more susceptible to hemolysis, and therefore have a shortened lifespan.

2. Description of the Related Art

Despite the fact that the cause of sickle cell disease (i.e., the very minor structural variation in the mutant hemoglobin) has been known for many years, little progress has been made in suitable treatment of the disease. Presently, the major treatment for the painful crises is medication for relief of pain, which merely treats the immediate symptoms. Tissue damage, often involving major organs, occurs with each successive episode of oxygen deprivation, and the cumulative effects of the disease are debilitating.

Several attempts have been made in the past to treat and manage sickle cell disease chemotherapeutically, but all have resulted in serious adverse health conditions. Many physiological laws have been applied biochemically in order to achieve success in this regard, but all efforts were frustrated by gross side effects. Examples of such attempts include the transformation of hemoglobin to carboxyhemoglobin (Sirs, J. A. "Preliminary Communication: The Use of Carbon Monoxide to Prevent Sickle-Cell Formation." *Lancet*, 971-972 (1963)), acetylation of hemoglobin molecules with aspirin; Shamsuddin, et al, "Sites of Acetylation of Sickle-Cell Hemoglobin by Aspirin," *Proc. Nat'l Acad. Sci.*, 71:43 (1975)), cross-linking hemoglobin molecules with dimethyl-adipimidate (Lubin, B. H. et al., "Dimethyl Adipimidate. A New Antisickling Agent." *Proc. Nat'l Acad. Sci.*, 72:43 (1975); Waterman M. R., et al., "Antisickling Nature of Dimethyl Adipidimate" *Biochem. Biophys. Res. Commun.*, 63:580 (1975)), and the use of carbonic anhydrase inhibitors (Hilowitz, G., "Sickle-cell Disease: New Method of Treatment, Preliminary Report," *Br. Med. J.*, 2:266 (1975)).

Other antisickling agents have been employed; however, their disadvantages have by far outweighed their advantages in the treatment of sickle cell disease. Some examples of such agents include urea, cyanate, procaine, pyridoxine, phenothiazines, steroids, nitrogen mustard, and 3,4 dihydro-2,2,-dimethyl-2H-1-benzopyran-6-butyric acid.

Over the years there has been much interest in the anti-sickling effects of roots from the tree *Fagara zanthoxyloide*, the genus of which Fagara contains over 100 different chemical compounds. In 1975, Sofowora, et al. reported the isolation and in vitro nonsickling characteristics of 2-hydroxymethylbenzoic acid which he and his co-workers extracted from the *Fagara zanthoxyloides* root. (Sofowora, et al. *Lloydia*, 38: 169-171 (1975)). In that same year, Honig et al. reported the in vitro effect of the aqueous Fagara extract described by Sofowora et al. above on the oxygen affinity and erythrocyte sickling in samples of whole blood from sickle cell patients. (Honig et al., *Lloydia*, 38:387-390 (1975)).

In 1977, Fadulu, the inventor of the present patent application, reported the in vitro anti-sickling effect of an extract of the *Fagara zanthoxyloides* root obtained from extraction with benzene, chloroform, ethyl acetate, and ethyl alcohol (Fadulu, Faculty Research Journal, 20-31 (1977). The chemical characteristics of the extract described in Fadulu's article suggested the presence of compounds similar in activity and structure to naturally occurring anesthetics. It was also observed from the IR spectrum that the extracted compound contained free sulfhydryl groups which were further hypothesized to play a role in its anti-sickling activity.

In addition to the Fagara root, other plants have been reported to contain compounds having in vitro antisickling properties. U.S. Pat. No. 4,473,559 to Robinson, for example, suggests in vitro anti-sickling properties of a mixture of compounds derived from porphyrinic or chlorophyllic compositions. U.S. Pat. No. 3,102,891 to Allen is incorporated by reference in Robinson and describes the extraction process for isolating the foregoing compound.

Other compounds have been reported to affect the levels of fetal hemoglobin (HbF), which has been found to ameliorate the clinical course of sickle cell disease. The first attempt to manipulate this change was by the use of 5-azacytidine, a cytotoxic agent. Administration of this agent increased HbF levels in sickle cell patients. Other cytotoxic agents such as cytosine arabinose, hydroxyurea, and hematopoietic factor erythropoietin have demonstrated similar effects. In a recent clinical trial, Perrine et al. reported rapid stimulation of the HbF following the administration of arginine butyrate (*N. Engl. J. Med.*, 328:81 (1993)). However, while these drugs that increase HbF hold promise in the therapy of sickle cell disease, clinical response to these drugs has not been impressive. Thus, a potentially effective drug for treating sickle cell disease or thalassemia would normalize the concentration of HbF to therapeutic levels.

Based on current knowledge of sickle cell disease, it appears feasible to develop a drug which will alleviate all of the symptoms of the disease and provide perfectly normal lives and life-expectancies for sickle cell patients. This drug would not cure the disease (because it is genetic in origin), but should effectively treat the disease by alleviation or prevention of its symptoms. The requisite capabilities of a potentially useful drug have been defined by the Sickle Cell Disease Branch of the United States National Institutes of Health (NIH). The requirements are specified in terms of several laboratory bioassays providing seven parameters that a candidate drug must meet.

Many drugs are known which are effective in normalizing one or more of these parameters, and fifteen of the most promising ones have been evaluated thoroughly (in vitro) by R. L. Nagel's group (*Blood*, 61:693 (1983)). However, as shown by Nagel, no one drug is capable of normalizing all seven parameters. Nagel's retrospective study thus explains the prior clinical failures of these drugs.

The extract of the present invention, however, displayed excellent responses in all these bioassays, as can be seen in the examples below. The effectiveness of the inventive extract in all seven U.S. NIH tests sets it apart as the only known extract which fulfills all of the in vitro requirements judged to be essential for a truly effective anti-sickling drug.

SUMMARY OF THE INVENTION

The present invention relates to compositions and methods of treating various hemoglobinopathies, particularly thalassemia and sickle cell disease, by administering a novel extract obtained from certain plant materials.

In the 1970's, Fadulu reported that the extract of the African chewing stick, prepared from the roots of the tree *Fagara zanthoxyloide*, possessed anti-sickling properties in in vitro studies. Chemical studies were initiated to isolate and identify the active compound(s) in the extract responsible for this activity. Ethyl alcohol extracts, for example, were reported to contain chemical compounds having free sulfhydryl groups. Fadulu, *Faculty Research J.*, 26-31 (1977). Since that time, systematic fractionation of this extract using different extraction and purification techniques, coupled with bioassay of the fractions produced at each state, ultimately led to the present isolation of a small amount of an extract, the invention extract, of non-polar compounds different from those extracts previously reported. This invention extract showed good activity in the blood-agar plate test developed by Fadulu to test for anti-sickling drugs.

The present invention also relates to the discovery of other plant materials which also contain the inventive extract comprising compounds possessing superior antisickling activity. These plant materials include alfalfa, hay, mustard greens, spinach, oak leaves, and grass clippings. Of all the foregoing plant materials, alfalfa is the most preferred due to its greater availability as well as its possessing a greater proportion of the active compounds.

Further, the present invention relates to improved extraction and purification techniques for obtaining the inventive extract from certain plant materials.

The present invention is unique, compared to existing treatments for sickle cell disease, in that the extract of the inventive method is the only one that satisfies all seven of the in vitro requirements set forth by the Sickle Cell Disease Branch of the NIH. Further, in vivo testing of the drug confirmed its efficacy in treating sickle cell disease by preventing the pathological manifestations associated with this disease. The inventive extract was also found to normalize HbF levels in patients suffering from sickle cell disease and thalassemia. Consequently, the subsequently disclosed results are indicative of the present invention's superiority to already existing treatments for these devastating and fatal diseases.

DETAILED DESCRIPTION OF THE PREFERRED EMBODIMENT

Figure 1:
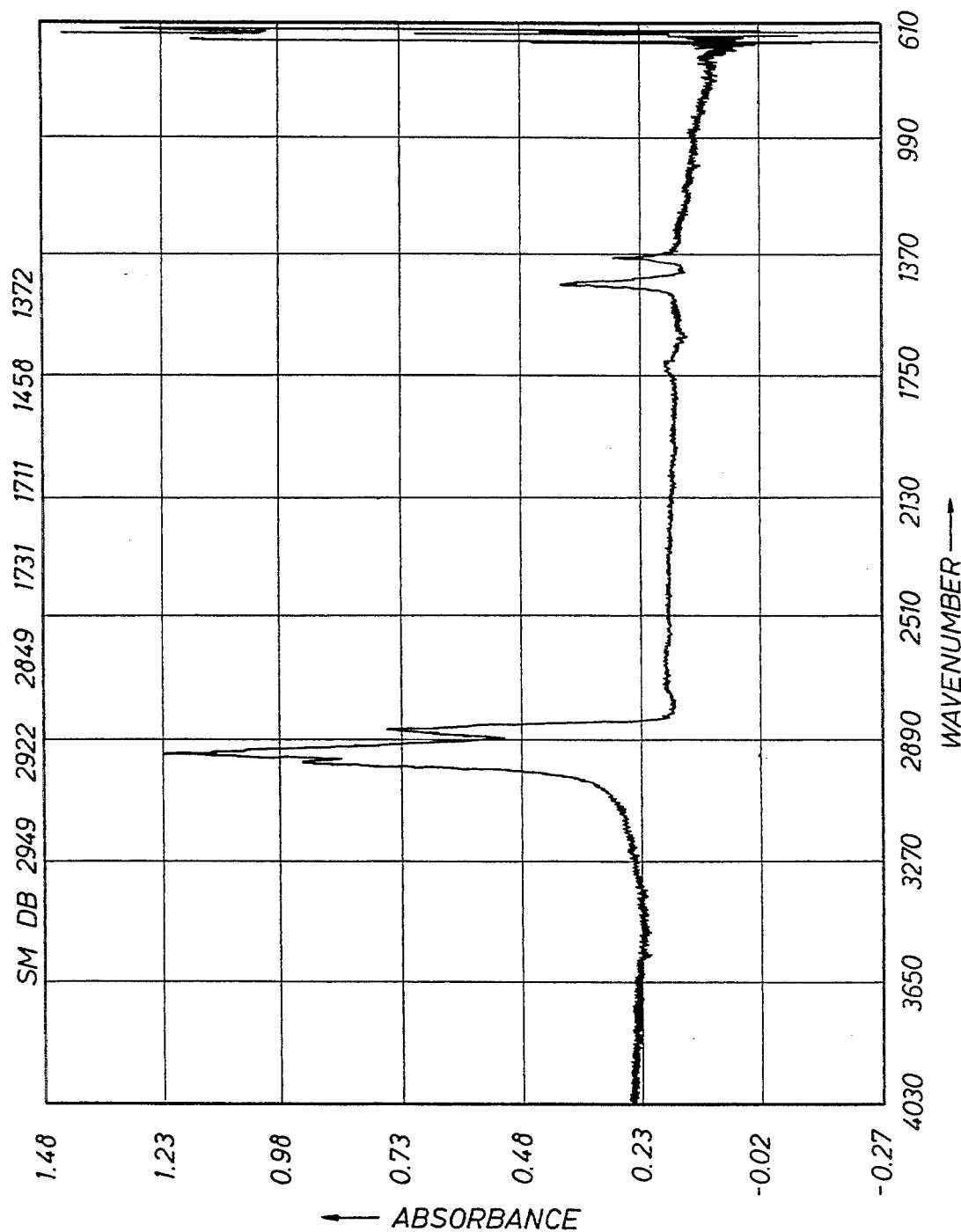
FIG. 1 is an infra red analysis trace of the invention extract showing peaks representing chemical compounds.

The invention is of an extract that is effective in the treatment of hemoglobinopathies, particularly sickle cell disease and thalassemia, and that meets all seven of the parameters set by the U.S. NIH. The invention method of treatment comprises the administration of the extract in effective dosage levels.

The Inventive Extract

While the actual active components of the extract have not yet been fully isolated and identified, it was found that the active anti-sickling components of the extract were the more polar components of non-polar acids. The less polar acids, which included stearic, linolenic, linoleic, and oleic acids, were found to have little if any anti-sickling activity.

The extract of the present invention is different from previous extracts reported to have been obtained from the Fagara root and other plant materials such as grasses and legumes, for example. The term "invention extract," refers to the mixture containing the active compounds (i.e., the more polar acidic compounds having significant anti-sickling activity) obtained from certain plant materials by the specific processes described herein. The physical analytical data known about the inventive extract thus far are as follows: IR: C—H symmetric stretch and asymmetric stretches; C=O stretch; C—H bending motion, low molecular weight aliphatic hydrocarbon (alkoxide) polyunsaturated-as shown in FIG. 1.

Sources of Extract

The extract of the present invention was first discovered from extracts of the Fagara root (i.e., *Fagara zanthoxyloides*); however, because this plant is difficult to obtain in adequate quantities, alternative plant materials were sought and discovered. These plant materials include alfalfa (*Medicago bativa*), hay (legumes), mustard greens (*Brassia balba*), spinach (*spinach oleracea*), oak leaves (Quercus), and grass clippings. Of all these plant materials, alfalfa contains the greatest proportion of the most polar compounds comprising the inventive extract. Next to alfalfa, hay contains a large proportion of the active acidic compounds, followed by the Fagara root. The remaining four plant materials contain lesser quantities of the desired more polar compounds comprising the inventive extract, with oak leaves containing the least. Because alfalfa contains the greatest proportion of the active compound, in addition to its ready availability year round, alfalfa is the most preferred plant material for the inventive extraction method, particularly for purposes of commercial scale-up requiring large quantities of plant material.

Extraction Method

For ease of explanation, the invention extraction method for obtaining the invention extract is explained with reference to alfalfa. This method, with minor variations depending upon the source, can also be used to obtain the extract from other sources disclosed herein.

Commercial alfalfa is available in bags in a finely divided dried form as well as in the familiar field-dried bales. In the preferred embodiment, the desired acid fraction (i.e., the fraction comprising the inventive drug) was obtained by soaking the alfalfa in about a 2 to about a 5%, preferably about 3%, aqueous sodium hydroxide solution (in a covered vessel) for a time sufficient enough to allow the active free acidic compounds in the plant material to dissolve in the base. The soaking time may be from about 0.5 hours to about 6 hours, preferably 2 hours. Generally speaking, all basic materials are suitable for the extraction process. These basic materials are exemplified by ammonium hydroxide and other halide hydroxides, such as potassium hydroxide and the like. The resulting hydroxide mixture is then filtered, preferably through a Dacron filter. After filtration, the resulting filtrate is washed thoroughly with water at least once. This washing step preferably comprises adding an amount of water sufficient to cover the filtrate, and then allowing the filtrate to stand for about 30 to about 60 minutes, after which the water is allowed to drain through a filter. The washed filtrate is then acidified to a pH of from about 1 to about 3 by slowly adding 50% of an acid, preferably sulfuric acid, with ice cooling and vigorous stirring. Other acids that may be employed for the acidification step include hydrochloric acid. Upon acidification, the filtrate becomes a pale brown or tan milky turbid suspension due to the separation of active acidic compounds which are insoluble in the acidic solution.

After acidification, the filtrate is extracted with an organic solvent selected from the group consisting of hexane, 1,1,1-trichloroethane (TCE), chloroform, and methylene chloride. Extraction with hexane comprises adding about 50 w/w % hexane to the filtrate and then shaking the mixture for about 0.5 hr. Following the slow separation of an emulsion that is difficult to break, the hexane layer, which selectively dissolves the active acidic compound, is removed, and the aqueous layer may be extracted again with the same amount of hexane as used before. The hexane layers are combined (if more than one extraction is performed) and dried over sodium sulfate. The hexane solvent is removed from the solution by distillation at reduced pressure using a rotary evaporator, for example, to yield a concentrated brownish oily residue comprising the active acids as well as other pigments. Small traces of water may be removed from the residue by adding a small amount of isopropyl alcohol, for example, and then removing the alcohol by distillation as previously described. If water is still present, the foregoing process may be repeated as necessary. If only one extraction with hexane performed, a yield of about 0.32% may be obtained. If two additional extractions are performed, the percent product yield may be increased to about 0.96%.

Originally, hexane was the solvent of choice because of its ability to dissolve selectively the active acidic compounds, leaving other acidic material behind. However, as mentioned above, its use is accompanied by severe emulsion problems. Thus, the more preferred solvents for extraction include TCE, chloroform, and methylene chloride, with TCE being the most preferred solvent, for reasons discussed below.

While extraction with TCE considerably reduces the emulsion problems that occur when hexane is used as the sole extracting solvent, TCE also removes large quantities of inactive acidic material. Thus, extraction with TCE involves additional extraction steps in order to separate the desired acidic compounds from the other unwanted inactive acids. However, in spite of the additional steps required, extraction with TCE is a more rapid process than direct hexane extraction, thus making it the more preferred extraction method, especially for large scale preparation.

Extraction with TCE comprises adding about 50 w/w % of TCE to the acidified filtrate and shaking the mixture for about 0.5 hr. Substantially all of the acidic compounds dissolve into the TCE layer, which is then removed and filtered to break the emulsion. The clear TCE phase is again separated and concentrated to remove TCE solvent. The acidic residue is then further extracted with about 50–150gm/100ml methanol, about 10–30 w/w % of water acidified to pH 2–4 with hydrochloric acid, and about 60–100 w/w % hexane in order to separate the active acids from the inactive acids (step 1). Following vigorous shaking, the hexane layer is separated (step 2), and the aqueous methanol layer is extracted as above with four more portions of hexane (each portion about ⅓ less than that used in step 1) (step 3). The aqueous methanol layer may be extracted additional two to six times, preferably four, by adding another portion of acidified water, followed by hexane as described in step 1 of the first extraction. After vigorous shaking and removal of the separated hexane layer, the aqueous methanol layer may be extracted at least two more times, preferably four more times, with the same amount of hexane as described in step 3 above. The hexane layers are combined (if more than one extraction is performed), and the hexane solvent is removed as described above for the direct hexane extraction method. One extraction of the acidic residue with acidified water/methanol/hexane results in about a 30–40% yield of product. If two to four additional extractions are performed, the percent product yield may be increased to about 80–95%.

In actual tests of both of the foregoing extraction methods (i.e., direct hexane extraction and TCE/methanol/hexane extraction), the active acidic compounds obtained in the final hexane fractions were found to be identical by thin layer chromatography (TLC). Removal of the hexane solvent as described earlier resulted in a brown-green oily mixture of the inventive acidic compounds which displayed good anti-sickling activity in the blood-agar test. The oily mixture is a fluid material of medium viscosity which pours readily and possesses a very mild odor similar to that of green plants.

Purification of the oily mixture, however, was hindered by the presence of significant quantities of dark pigments which co-chromatographed with the desired acids. These pigments may be removed by partitioning an ethyl acetate solution of the hexane acids into three fractions, one of which is extractable by 5% sodium bicarbonate, the second fraction which is extractable by 5% sodium carbonate, and the third fraction which is extractable by neither. The third fraction, which was soluble in neither bicarbonate or carbonate, was not significantly active. Most of the interfering pigments were found in the bicarbonate fraction, whereas the carbonate fraction was mostly pigment-free. The yellow carbonate fraction was strongly active in the blood-agar plate test, and TLC showed a predominance of the characteristic spots associated with the active acidic compound. The bicarbonate fraction was less active and showed the presence of some of the desired components, but the TLC pattern was strongly overlaid by a continuous streak of pigments.

Since the purified carbonate fraction contained primarily the more active acidic compounds possessing anti-sickling activity, it was the source of material for in vitro hematologic studies, the results of which are summarized in Examples 4–12 below.

Efficacy of the Inventive Extract and Dosage Levels

The relevant hematology studies, as defined by the U.S. Sickle Cell Disease Branch of the NIH, address the following seven parameters in which red blood cells or the hemoglobin from sickle cell patients display abnormal behavior characteristic of the disease: (1) oxygen equilibrium, (2) concentration of 2,3-diphoshoglycerate (2,3-DPG), (3) cell indices, (4) solubility of deoxyhemoglobin, (5) osmotic fragility, (6) kinetics of sickling, and (7) reversibility of sickling.

Another useful bioassay measures the concentration of total and free intracellular calcium ion concentration. Aside from meeting all the NIH requirements, the inventive extract's ability to inhibit the sickling process was further demonstrated in an in vitro bioassay showing its effect on the concentration of free intracellular calcium. (See Example 12).

In each of the foregoing in vitro tests, the extract of the present invention was effective in reducing or eliminating the abnormal behavior to the extent that the measured parameters of treated sickle cell blood were very close to, or in some instances the same as, those of blood from normal blood donors, which served as controls.

For in vivo administration, the inventive extract may be incorporated in an acceptable pharmaceutical formulation suitable for all dosage forms, including oral, parenteral, and rectal formulations. The inventive extract is readily absorbed from all three routes of administration. Oral formulations include tablets, capsules, syrups, suspensions, elixirs, and sublingual or buccal dosage forms. Parenteral formulations include intramuscular and intravenous injections, and rectal formulations include suppositories, ointments, and creams. Other formulations include nasal, subcutaneous, and transdermal dosage forms. The excipients that may be employed in all of the formulations are those typically known by those of ordinary skill in the art.

The dosage for each formulation is an amount sufficient to elicit the desired therapeutic effect in the treatment of hemoglobinopathies such as the sickle cell diseases and thalassemia, for example. In oral administration, for example, the daily dosage range is from about 6.25 mg to about 200 mg of the extract, administered once daily or divided in two or three doses, depending upon the patient profile and the type of pharmaceutical formulation employed. In treating thalassemia and sickle cell patients, the preferred therapeutically effective amount administered daily is from about 12.0 mg to about 150 mg of the extract, preferably divided into three doses. The more preferred daily doses range from about 50 mg to about 100 mg, preferably divided in three doses, with the most preferred therapeutic amount administered daily being about 75 mg of the extract, preferably administered in three divided doses.

A preferred pharmaceutical formulation of the present invention for oral administration, especially in children, is a syrup comprising the following components: the inventive extract, preferably obtained from alfalfa; about 60–90 w/w % solution of sorbitol in water; methylparaben; propylparaben; Tween 80; erythrosin B; and optionally a flavoring ingredient, such as cherry flavoring, for example. The components are mixed together at room temperature, by conventional methods commonly known by those of skill in the art, for about twelve hours. The preferred dose of the syrup is from about one to about three teaspoonsful per day, preferably three per day. The components are mixed in such proportions that each teaspoonful (i.e., 5 ml.) contains 25 mg of the inventive extract, 5 mg methylparaben, 2.5 mg propylparaben, 5 mg Tween 80, 5 mg erythrosin B, and 0.005 ml of cherry flavoring, for example, all of which are dissolved or dispersed in a 70 w/w % solution of sorbitol in water.

The following examples do not limit the scope of the invention, but are intended to illustrate aspects of the invention.

EXAMPLE 1

Extraction of Acids—Laboratory Scale

Dried, finely ground alfalfa used in laboratory studies was purchased in 50-lb bags from commercial feed stores.

500 gm of alfalfa were mixed thoroughly with 1 liter of 3% aqueous sodium hydroxide and allowed to stand for 3 hours. The mixture was filtered through a Dacron filter of Pellon fleece, and the resulting filtrate was washed thoroughly with water. The clean filtrate was acidified to pH 1–3 by slow addition of 50% sulfuric acid with ice cooling and vigorous stirring. The milky solution was then shaken in a separatory funnel with 250 ml of hexane. Following the slow separation of a serious emulsion and removal of the hexane, the aqueous layer was extracted twice more with 250 ml of hexane. The combined hexane extracts were dried over sodium sulfate, and then distilled using a Rotovap at 40° C. at water pump vacuum. Final traces of solvent were removed at 1 mm Hg, leaving a brown oil weighing 480 mg (0.96% yield). This product was referred to as the "hexane fraction."

EXAMPLE 2

Extraction of Acids—Pilot Scale

Standard bales of alfalfa from commercial feed stores were employed for large scale extractions.

Because of its much lower bulk density, bale alfalfa required larger relative volumes of liquid than the bag alfalfa, discussed in Example 1, to completely cover it for extraction. Thus, for 10 kg of bale alfalfa, 20 gal of 3% sodium hydroxide was needed. After standing for 2 hours at room temperature, the aqueous phase was removed through a Dacron filter, and the residual alfalfa was washed with water. The water was then removed through a filter. The aqueous filtrate was acidified to pH 1–3 with sulfuric acid and then extracted with a total of 6 gal. of hexane. Clear hexane layers were separated, and residual emulsions were broken by filtration through Celite, affording an additional hexane layer which was combined with the first. The mixture was then dried over sodium sulfate, and the hexane solvent was removed, as discussed in Example 1, to yield 8 to 9 gm. of hexane fraction. This represented 83 to 93% of the yield obtained on the laboratory scale.

EXAMPLE 3

Preferred TCE Extraction of Acids—Pilot Scale

Following acidification of the aqueous filtrates, as discussed in Example 2, the aqueous phase was extracted with a total of 2 gal. of TCE, which dissolved all acidic compounds and segregated them into a separate layer. This layer was separated, filtered through filter paper to break the emulsion, and the clear TCE phase was again separated. The mixture was then dried over sodium sulfate, and the TCE solvent was removed as discussed in Example 1. The acidic residue obtained at this point weighed about 20 gm (from 10 kg of plant material).

This residue was treated as follows to separate the desired hexane soluble portion of the extract:

The acidic residue was dissolved in 100 ml of methanol and placed in a separatory funnel. 20 ml of water acidified with hydrochloric acid to pH 2–4 and 150 ml of hexane were then added to that solution. Following vigorous shaking, the hexane layer was separated. The aqueous methanol layer was extracted as above four times with 100-ml portions of hexane. Another 30 ml of acidified water was then added to the aqueous methanol layer, followed by 100 ml of hexane. Following vigorous shaking, the hexane layer was separated. The aqueous methanol layer was extracted with four more 100-ml portions of hexane. Another 50 ml of acidified water was added to the aqueous methanol layer, followed by 75-ml of hexane. Following shaking, the hexane layer was separated. The aqueous methanol layer was extracted again with four more 75 ml portions of hexane. All of the hexane extracts were combined, decanted from a small amount of insoluble material, and concentrated in vacuo to remove all of the hexane, leaving about 9 gm of the desired active acidic compounds.

EXAMPLE 4

Bioassay 1: The Effect of the Inventive Extract on Oxygen Equilibrium

In this bioassay, the oxygen affinity of HbS blood at various pH's, particularly pH 7.2–7.4, in the presence of the inventive drug was studied. Such information was useful in light of current knowledge that some potential anti-sickling agents were found to act primarily by increasing the oxygen affinity of hemoglobin while other experimental agents may directly inhibit polymerization of deoxyhemoglobin in HbS blood.

Various concentrations of the inventive extract were tested to measure the effects of different pH's on the oxygen affinity of whole blood from sickle cell patients at 37° C. and constant $CO_2$ tension of 40 mm Hg.

Blood samples were prepared according to the method of Harrington and Nagel as described in *J. Lab. Clin. Med.*, 90:863–872 (1977). For measurements of oxygen equilibria, 6 ml of blood were equilibrated in a tonometer at 37° C. with 5.6% $CO_2$ in oxygen ($pCO_2=40$ mm Hg). Whole blood pH (pHE), intra-cellular pH (phi), and blood $pO_2$ measurements were then made according to the procedures of Y. Ueda, R. L. Nagel, and R. M. Bookchin, *Blood*, Vol. 53, No. 3, pp. 473–480 (1979).

The mean values and range of baseline measurements on the normal blood and sickle cell blood samples are shown in Table 1. Since the behavior of hemoglobin depends upon its immediate intracellular environment, the difference between HbS red blood cells and normal (i.e., HbA) red blood cells, especially the red blood cell 2,3-DPG concentrations with the corresponding lower-than-normal intracellular pH (pHI) levels, was considered in evaluating the inventive extract. Thus, the oxygen affinity was analyzed with reference to both whole blood pH (pHE) and intracellular pH (pHI) measured at each point in the determinations of HbS blood treated with various concentrations of the inventive extract.

TABLE 1

Control data of all blood samples from normal donors and sickle cell patients used. Values for each sample were averaged. The group mean ± SD was determined. The ranges of values are in parenthesis.

|  | Normal Blood (10 Samples) | Sickle Cell Blood (30 Samples) |
|---|---|---|
| *HGB (g/dl) | 14.2 ± 1.0 | 7.2 ± 1.4 |
|  | (15.0–14.05) | (5.8–8.5) |
| Hct (%) | 44.3 ± 1.1 | 20.2 ± 2.1 |
|  | (45.4–44.1) | (19.1–23.1) |
| MCV ($mm^3$) | 90 ± 9 | 88.3 ± 3.0 |
|  | (90–99) | (85.2–91.3) |
| MCH (mmg) | 29 ± 2 | 29.3 ± 2.5 |
|  | (27.5–31) | (35.0–38.0) |
| MCHC (g/dl) | 35 ± 2 | 36.7 ± 3 |
|  | (32.3–36.8) | (35.0–38.0) |
| **HGBF (% of total HGB) | — | 2.54 ± 1.0 (1.54–2.6) |

*HGB = Hemoglobin
**HGBF = Hemoglobin F

Control data showing oxygen affinities (whole blood=$p_{50}E$ and intracellular=$p_{50}I$) of normal HbA blood and HbS blood with changes in pH are shown in Table 2. Table 3 illustrates the affinities of treated HbS blood (i.e., treated with various concentrations of the inventive drug), untreated HbS blood, and normal HbA blood with changes in pH. These values were in agreement with previously reported values (E. Bursoux, A. Freminet, and C. F. Puyart, *Bull. Physio-Path. Resp.*, 8:755–767 (1972); Y. Ueda, R. L. Nagel, and R. M. Bookchin, *Blood*, Vol. 53, No. 3, pp. 473–480 (1979). The values for normal red blood cells varied little over the pH range studied. In the HbS blood samples, the oxygen affinity was significantly lower than normal (i.e., higher $p_{50}$ values). However, HbS blood incubated with the inventive extract demonstrated a remarkable similarity to normal blood values, especially HbS blood samples containing drug concentrations of 25 μg/ml.

TABLE 2

Control data on some blood samples from normal donors and sickle cell disease patients used in the study. The values in parentheses represent the log $p_{50}$. The $p_{50}$ values represent the average of the three samples of normal blood and the six samples of sickle cell blood.

|  | $p_{50}I$ | $p_{50}E$ |
|---|---|---|
|  | Normal Blood (3 Samples) | |
| pH 6.8 | 37.3 (1.57) | 37.3 (1.57) |
| pH 7.0 | 34.0 (1.53) | 33.0 (1.52) |
| pH 7.2 | 30.2 (1.47) | 31.0 (1.49) |
| pH 7.4 | 26.5 (1.42) | 28.6 (1.46) |
| pH 7.6 | — | 24.0 (1.38) |
|  | Sickle Cell Blood (6 Samples) | |
| pH 6.8 | 55.0 (1.75) | 48.4 (1.68) |
| ph 7.0 | 51.9 (1.72) | 44.7 (1.65) |
| pH 7.2 | 40.6 (1.69) | 37.2 (1.57) |
| pH 7.4 | 32.9 (1.52) | 31.0 (1.49) |
| pH 7.6 | — | 28.3 (1.45) |

TABLE 3

Data on normal blood samples, untreated sickle cell blood samples, and sickle cell blood samples treated with four concentrations of the inventive extract. These data show both intracellular ($p_{50}I$) and extracellular ($p_{50}E$) partial pressures.
A = Untreated sickle cell blood at time 0.
B = Untreated sickle cell blood at 2 hours.
C = Treated sickle cell blood (15 μg/ml).
D = Treated sickle cell blood (25 μg/ml).
E = Treated sickle cell blood (50 μg/ml).
F = Treated sickle cell blood (100 μg/ml).

|  | Normal Blood $p_{50}I$ | Normal Blood $p_{50}E$ |
|---|---|---|
| pH 6.8 | 37.3 | 37.3 |
| pH 7.0 | 34.0 | 33.0 |
| pH 7.2 | 30.2 | 31.0 |
| pH 7.4 | 26.5 | 28.6 |

|  | A | B | 15 μg C | 25 μg D | 50 μg E | 100 μg F |
|---|---|---|---|---|---|---|
|  | Sickle Cell Blood $p_{50}I$ | | | | | |
| pH 6.8 | 49.0 | 50.0 | 49.3 | 37.2 | 48.0 | 38.0 |
| pH 7.0 | 45.0 | 48.0 | 37.4 | 34.3 | 43.0 | 30.6 |
| pH 7.2 | 32.0 | 35.2 | 35.0 | 29.9 | 31.2 | 25.0 |
| pH 7.4 | 30.1 | 32.5 | 28.5 | 27.0 | 23.0 | 22.6 |
|  | Sickle Cell Blood $p_{50}E$ | | | | | |
| pH 6.8 | 48.4 | 50.0 | 48.5 | 37.0 | 49.0 | 40.0 |
| pH 7.0 | 44.7 | 45.0 | 38.1 | 34.1 | 44.0 | 36.0 |
| pH 7.2 | 37.2 | 37.8 | 34.0 | 30.8 | 35.0 | 24.9 |
| pH 7.4 | 31.0 | 33.0 | 30.0 | 27.5 | 22.5 | 24.5 |

EXAMPLE 5

Bioassay 2: The Effect of the Inventive Extract on 2,3DPG Concentrations

Preliminary preparations of blood samples were carried out as described in Example 4. Concentrations of red blood cell 2,3-DPG were determined by the method of Z. B. Rose and J. Liebowitz, *Anal. Biochem.*, 35:177–180 (1970), using a Sigma 35-UV kit and a Gilford Model 240 spectrophotometer. Different concentrations of the extract were used, as shown in Table 4, and the samples were incubated at 37° C. for 2 hours. The extracellular pH at $P_{50}$ ($pH_{50}E$) and intracellular pH at $P_{50}$ ($pH_{50}I$) were maintained at 7.4 and 7.3, respectively. The levels of 2,3-DPG were determined.

The mean values and ranges of baseline measurements in the HbA and HbS blood samples are shown in Table 5. At blood pH levels of 7.4, most of the low oxygen affinity of HbS blood can be attributed to the increased levels of 2,3-DPG, which leads to the lower intracellular pH of HbS red blood cells. Thus, the levels of 2,3-DPG were analyzed with reference to extracellular ($pH_{50}E$) and intracellular pH ($pH_{50}I$) of HbS blood incubated with various concentrations of the inventive extract at 37° C. for 2 hours. Levels of 2,3-DPG of normal HbA blood and HbS blood treated with various concentrations of the inventive drug are shown in Table 4 along with the corresponding $pH_{50}E$ and $pH_{50}I$ values. In untreated HbS blood, the level of 2,3-DPG was significantly higher than that of normal red blood cells. However, HbS blood containing 25 μg/ml of the inventive extract demonstrated 2,3-DPG levels similar to those levels in the normal blood sample.

TABLE 4

Data on 3 normal (HbA) blood samples and 6 sickle cell (HbS) blood samples showing the levels of 2,3-DPG and $p_{50}$ at particular extracellular ($pH_{50}E$) and intracellular ($pH_{50}I$) pH's ($pH_{50}$ = pH at 50% oxygen saturation). $p_{50}$ denotes the oxygen tension at which blood samples were half saturated with oxygen under the

TABLE 4-continued experimental conditions described.
N = Normal Blood
A = Untreated sickle cell blood at 0 hours.
B = Untreated sickle cell blood incubated at 37° C. for 2 hours.
C = Treated sickle cell blood (15 μg/ml), incubated at 37° C. for 2 hours.
D = Treated sickle cell blood (25 μg/ml), incubated at 37° C. for 2 hours.
E = Treated sickle cell blood (50 μg/ml), incubated at 37° C. for 2 hours.
F = Treated sickle cell blood (100 μg/ml), incubated at 37° C. for 2 hours.

|  | N | A | B | 15 μg C | 20 μg D | 50 μg E | 100 μg F |
|---|---|---|---|---|---|---|---|
| 2,3-DPG | 14.3 | 20.2 | 24.3 | 24.0 | 15.2 | 11.8 | 11.3 |
| pH$_{50}$E | 7.40 | 7.30 | 7.20 | 7.20 | 7.41 | 7.43 | 7.48 |
| pH$_{50}$I | 7.30 | 7.10 | 7.05 | 7.06 | 7.28 | 7.35 | 7.35 |
| p50 (mm Hg) | 27.50 | 34.0 | 42.5 | 42.0 | 28.0 | 24.8 | 24.6 |

TABLE 5

Control data on blood samples from normal donors and sickle cell disease patients used in the study. pH$_{50}$ extracellular denotes the pH of whole blood at the half saturation point, while pH$_{50}$ intracellular denotes the pH of washed and lysed red blood cells (values extrapolated from measurements refer to pH at the half saturation point).

|  | Normal Blood (3 Samples) | Sickle Cell Blood (6 Samples) |
|---|---|---|
| 2,3-DPG (μMoles/g HGB) | 14.5 ± 1.3 (13.0–15.6) | 20.3 ± 1.0 (19.8–21.0) |
| pH$_{50}$ extracellular | 7.40 ± 0.02 (7.38–7.43) | 7.35 ± 0.03 (7.32–7.40) |
| pH$_{50}$ intracellular | 7.28 ± 0.03 (7.25–7.30) | 7.12 ± 0.05 (7.10–7.24) |
| p50 (mm Hg) | 26.4 ± 1.5 (25.6–28.4) | 31.9 ± 1.8 (30.8–33.2) |

EXAMPLE 6

Bioassay 3: The Effect of the Inventive Extract on Red Blood Cell Indices

Blood samples were treated as described in Example 4. Control values on ten normal HbA blood samples and thirty HbS samples are shown in Table 1. These are the mean values and ranges which serve as the baseline measurements. Table 6 shows the results of treated and untreated HbS blood samples. Various concentrations of the inventive extract (15 μg/ml–100 μg/ml) were used. The blood samples were incubated at 37° C. for 2 hours. The MCV (i.e., mean cell volume) of HbS cells treated with the inventive extract at the concentration of 25 μg/ml were closer to values of normal red blood cells, while the MCV of untreated HbS red blood cells decreased significantly. In some cases, the MCV of the treated HbS cells increased to as much as 103 mm$^3$. Similarly, MCH (i.e., mean cell hemoglobin) and MCHC (i.e., mean cell hemoglobin concentration) of the cells treated with inventive extract at concentrations of 25 g/ml were in the normal range.

TABLE 6

Data on normal blood samples, untreated sickle cell blood samples, and sickle cell blood samples treated with four different concentrations of the inventive extract (incubated for 2 hours at 37° C.).
N = Normal blood
A = Untreated sickle cell blood.
B = Washed untreated sickle cell blood cells resuspended in minimal essential medium (MEM) (solvent for the inventive extract).
C = Washed and treated sickle cell blood (15 μg/ml) resuspended in MEM.
D = Washed and treated sickle cell blood (25 μg/ml) resuspended in MEM.
E = Washed and treated sickle cell blood (50 μg/ml) resuspended in MEM.
F = Washed and treated sickle cell blood (100 μg/ml) resuspended in MEM.

|  | N | A | B | 15 μg C | 25 μg D | 50 μg E | 100 μg F |
|---|---|---|---|---|---|---|---|
| HGB (g/dl) | 14.2 | 7.2 | 5.8 | 5.8 | 7.3 | 7.1 | 5.6 |
| Hct (%) | 44.3 | 20.0 | 18.0 | 19.1 | 22.0 | 20.5 | 17.0 |
| MCV (mm$^3$) | 93.3 | 83.3 | 80.1 | 85.2 | 92.5 | 99.0 | 103.0 |
| MCH (mmg) | 29.0 | 31.2 | 31.6 | 31.7 | 29.2 | 30.1 | 31.9 |
| MCHC (g/dl) | 35.0 | 37.0 | 40.0 | 36.7 | 35.3 | 31.0 | 30.9 |

EXAMPLE 7

Bioassay 4: The Effect of the Inventive Extract on the Solubility of Deoxy Sickle Cell Hemoglobin (i.e., Deoxy HbS)

There is substantial evidence that the polymerization of deoxy HbS, which requires a high concentration of hemoglobin, substantially lowers its oxygen affinity. However, it has been discovered that some experimental anti-sickling agents may directly inhibit polymerization of hemoglobin. Consequently, examination of the solubility of HbS treated with the inventive extract is desirable in evaluating the it's efficacy as a potential anti-sickling agent.

Purified HbS was concentrated by ultrafiltration during dialysis against 0.1M KH$_2$PO$_4$ buffer, pH 7.35. For this bioassay, samples were prepared and deoxygenated according to the procedure of Hofricher, J., et al., *Pro. Nat'l. Acad. Sci. U.S.A.*, 4864–4866 (1974). The hemoglobin concentration of the deoxygenated samples was determined after conversion of aliquots to cyanmethemoglobin with Drabkins reagent, and the pH was measured with a Radiometer microelectrode. Each result was expressed as a relative solubility ratio; i.e., the supernatant concentration of the treated sample divided by that of the control (Adapted from Hofichter, et al. *Proc. Nat'l. Acad. Sci. U.S.A.* 73:3035–3039 (1976); and Noguchi and Schrecter, *Biochemistry*, 17: 5445–5459 (1978)). This bioassay was performed using only one concentration of the drug (25 μg/ml), and the results are shown in Table 7.

The control using HbS provided a supernatant having a pH in the range of 6.8–7.0 upon addition of sodium dithionite, and contained an average of 12.2 gm/dl hemoglobin at 25° C.. The corresponding supernatant for sickle cell hemoglobins treated with the inventive extract showed an average concentration of 22 gm/dl hemoglobin. Thus, the results indicated that the inventive extract enhanced the solubility of deoxy HbS, thereby substantially inhibiting gelation. Concentration/saturation (Csat), i.e., the minimum concentration of deoxy HbS needed for gelation, was measured in terms of relative solubility. The average relative solubility of 1.8, i.e., twice the solubility in the controls, was observed for deoxy HbS treated with the inventive extract. This value exceeded that (i.e., 1.6) of bis (3,5-dibromosalicyl) fumarate, the most effective gelation inhibitor reported in the literature (Chang, Ever, Bookchin, and Nagal, *Blood,* 6! (4): 693-704 (1983)).

TABLE 7

Data on deoxygenated sickle cell hemoglobin (HbS), untreated and treated with the inventive extract (25 μg/ml). Three samples of HbS were used in this study.

|  | Hb Conc. (g/dl) | pH | Supernatant Hb Conc. | Relative Solubility |
|---|---|---|---|---|
| Control | 20–25 | 6.8–7.0 | 10.2–12.5 | — |
| Deoxy Hb | 22.0 ± 2.0 | 6.9 ± 1.0 | 11.2 ± 1.0 |  |
| Deoxy Hb | 20–25 | 7.1–7.2 | 21.5–23.4 | 2.0 ± 0.2 |
| (25 μg/ml) | 22.0 ± 2.0 | 7.1 ± 1.0 | 22.0 ± 1.5 |  |

EXAMPLE 8

Bioassay 5: The Effect of the Inventive Extract on Osmotic Fragility

It is known that red blood cells containing HbS are significantly less fragile than normal red blood cells. Such an increased rigidity makes the membrane of these cells less capable of exuding calcium ions, thus causing an increase in membrane-bound intracellular calcium, which is thought to contribute to the sickling of the cells. Consequently, it is important to determine the effect of the present inventive extract on osmotic fragility of red blood cells in evaluating its efficacy as a potential anti-sickling agent.

Fresh untreated and treated red blood cells were diluted to a concentration of $2.5 \times 10^6$ cells/ml. Fragility of the HbS red blood cells and normal red blood cells was determined by placing the cells in graded series of hypotonic saline solutions. Concentrations ranged from 0.2% to 0.9% NaCl. Cells (0.1 ml) were placed into each tube ($2 \times 10^5$ cells), after which the tubes were slightly shaken and allowed to stand for 2 hours. The number of cells not lysed/saline concentration was determined by the use of a phase contrast microscope and a hemacytometer. Hemolysis was calculated using the following equation:

number of cells after 2 hours × 100/ number of cells inoculated

The HbS cells were treated with two concentrations of the inventive extract (25 μg/ml and 50 μg/ml) for 30 minutes. The results are shown in Table 8.

Osmotic fragility tests were performed on the HbS red blood cells and normal red blood cells before and after incubation. Unincubated (0 hour) HbS cells demonstrated decreased osmotic fragility compared to normal cells. Twelve percent of the unincubated HbS cells lysed only after exposure to 0.32% NaCl. In the most hypotonic saline solution (i.e., 0.20% NaCl), only 65% of the HbS cells were lysed.

Untreated HbS red blood cells incubated for 2 hours demonstrated osmotic fragility similar to that of 0-hour, unincubated HbS cells. 22% lysis of these cells occurred in the 0.30% saline concentration. Osmotic fragility of normal red blood cells also decreased under these conditions (i.e., 84% at 0.30% NaCl).

Incubation of HbS red blood cells in the presence of 25 μg/ml of the inventive extract, however, caused an increase in osmotic fragility closer to that of normal red blood cells. HbS cells showed a slight increase of fragility when exposed to 50 μg/ml of the inventive extract.

TABLE 8

Data showing the osmotic fragility of normal cells and sickle cells incubated for 2 hours at room temperature (25° C.). Osmotic fragility was also determined immediately (0 hour) after placing cells in saline solutions of various concentrations (% NaCl). Sickle cells treated with two concentrations of the inventive extract (25 μg/ml and 50 μg/ml) were incubated with the inventive extract for 30 minutes before being placed in the various saline solutions.

| % NaCl | % Lysis | | | | | |
|---|---|---|---|---|---|---|
|  | Normal 0 Hr | Normal 2 Hrs | Sickle 0 Hr | Sickle 2 Hrs | Sickle 2 Hrs (25 μg/ml) | Sickle 2 Hrs (50 μg/ml) |
| 0.20 | 100 | 100 | 65 | 72 | 100 | 100 |
| 0.28 | 100 | 93 | 38 | 40 | 100 | 100 |
| 0.30 | 100 | 84 | 25 | 22 | 90 | 100 |
| 0.32 | 100 | 60 | 12 | 10 | 80 | 100 |
| 0.34 | 88 | 30 | 4 | 2 | 72 | 100 |
| 0.36 | 78 | 18 | 1 | 0 | 50 | 100 |
| 0.38 | 65 | 14 | 0 | 0 | 30 | 88 |
| 0.40 | 40 | 4 | 0 | 0 | 15 | 65 |
| 0.42 | 22 | 0 | 0 | 0 | 0 | 40 |
| 0.44 | 13 | 0 | 0 | 0 | 0 | 28 |
| 0.50 | 4 | 0 | 0 | 0 | 0 | 15 |

EXAMPLE 9

Bioassay 6: The Effect of the Inventive Extract on the Rate of Sickling (i.e., Kinetics of Sickling)

Since the extract of the present invention significantly inhibits HbS gelation and has a positive effect on hemoglobin-oxygen affinity, it was necessary to determine its effect on the rate of sickling of HbS red blood cells. An effective anti-sickling agent increases the half-life of the sickling process as well as the delay time (i.e., the time between the application of stress and the onset of the rapid process of sickling). Such an agent also reduces the ultimate proportion of red blood cells which become sickled. (Harrington and Nagel, *J. Lab. and Clin. Med.*, 90:863–872 (1970)).

Ten milliliters of HbA and HbS whole blood were treated as in Example 4 with 25 μg/ml of the inventive extract and incubated for 30 minutes. No more than a 1:3 (v:v) ratio of drug solution to blood was used so that conditions similar to that of whole blood were maintained. Progressive deoxygenation of the blood with varying proportions of oxygen, nitrogen, and 5.6% carbon dioxide was carried out in a tonometer (model 1L237) at 37° C.. After 10 minutes equilibration with each gas mixture, the $pO_2$, the percent oxygen saturation (i.e., percent $O_2$, which is the amount of oxygen combined with the hemoglobin), and the pH were measured. Aliquots were transferred into buffered formalin for examination of cell morphology at different times, $pO_2$'s and pH's. The percentage of newly sickled cells was calculated using the following equation:

$$\% \text{ of sickle cells} = \frac{\# \text{ of sickled cells} - ISC}{\text{Total cells counted} - ISC}$$

Cells counted included normal, sickled, and irreversibly sickled (i.e., ISC) cells.

In this bioassay, the proportion of sickled red blood cells in test and control samples of normal blood was measured periodically over 120 minutes, after which time equilibrium was reached. Sickling processes were inhibited in the presence of a deoxygenating agent when HbS cells were incubated with 25 μg/ml of the inventive drug. As a result, the rate of sickling was reduced, and the delay time was increased. Within a period of 2 hours, 85% of the untreated deoxygenated HbS red blood cells became sickled, with a delay time of 30 seconds, whereas only 25% of the HbS cells treated with the inventive extract were sickled within the same time period and with a considerable increase in delay time of 20 minutes. The results of this bioassay are shown in Table 9.

TABLE 9

Kinetics of Sickling

| | Control | | |
|---|---|---|---|
| Time (min) | Normal Cells | Untreated Sickle Cells | Treated Sickle Cells |
| Blood Oxygen Tension (mm/Hg)* | | | |
| 0 | 0 | 0 | 0 |
| 10 | 10 | 10 | 10 |
| 20 | 20 | 20 | 20 |
| 30 | 30 | 30 | 30 |
| 40 | 40 | 40 | 40 |
| 50 | 50 | 50 | 50 |
| 60 | 60 | 60 | 60 |
| 70 | 70 | 70 | 70 |
| 80 | 80 | 80 | 80 |
| 90 | 90 | 90 | 90 |
| 100 | 100 | 100 | 100 |
| 110 | 100 | 100 | 100 |
| % Hemoglobin Saturation** | | | |
| 0 | 0 | 0 | 0 |
| 10 | 7 | 10 | 6 |
| 20 | 35 | 25 | 40 |
| 30 | 57 | 45 | 60 |
| 40 | 75 | 62 | 79 |
| 50 | 83 | 75 | 86 |
| 60 | 88 | 84 | 91 |
| 70 | 92 | 88 | 95 |
| 80 | 95 | 92 | 95 |
| 90 | 96 | 94 | 96 |
| 100 | 97 | 96 | 97 |
| 110 | 97 | 97 | 97 |
| % Sickled Cell | | | |
| 0 | 0 | 10 | 10 |
| 10 | 0 | 10 | 10 |
| 20 | 0 | 80 | 10 |
| 30 | 0 | 82 | 14 |
| 40 | 0 | 85 | 17 |
| 50 | 0 | 85 | 20 |
| 60 | 0 | 83 | 23 |
| 70 | 0 | 84 | 24 |
| 80 | 0 | 85 | 23 |
| 90 | 0 | 86 | 25 |
| 100 | 0 | 86 | 24 |
| 110 | 0 | 88 | 25 |

*$P_{50}E$ = $pO_2$ extracellular
**$P_{50}I$ = $pO_2$ intracellular

EXAMPLE 10

Bioassay 7: The Effect of the Inventive Extract on the Reversibility of the Sickling Process For this bioassay, the method of Harrington and Nagel, *J. Lab. Clin. Med.*, 90:863–872 (1977), was used. In this test, 10 ml of whole blood containing normal and HbS red blood cells were treated with sodium dithionite in order to initiate the sickling process by deoxygenation. Next, the red blood cells were treated with 25 μg/ml of the inventive extract in 10 ml of phosphate buffered plasma solution (pH 7.4) The extent of sickling and the different shapes were microscopically determined.

Table 10 shows that the extract of the present invention reversed the sickling by 92%, since 60% of the red blood cells, all of which were distorted in shape prior to treatment with the inventive extract, reverted back to normally shaped cells.

TABLE 10

| Sample | % Types of Shapes | % Reversibility |
|---|---|---|
| Whole Blood Type HbA | | |
| Normal Shape Cells | 99% | |
| Distorted Shape Cells | 1% | |
| Whole Blood Type HbS - Untreated | | |
| Normal Shape Cells | 35% | |
| Distorted Shaped Cells | 65% | |
| Whole Blood Type HbS-Treated 25 μg/ml | | 92% |
| Normal Shape Cells | 95% | |
| Distorted Shape Cells | 5% | |

EXAMPLE 11

Bioassay 8: The Effect of the Inventive Extract on the Inhibition of the Sickling Process (in vitro)

Both normal and sickled red blood cells are red in color when oxygenated, but turn brown in color when they become deoxygenated. This test was conducted to determine how much faster HbS red blood cells are deoxygenated as opposed to how slowly normal red blood cell are deoxygenated.

Three blood samples were prepared as follows: To one test tube was added 1 ml of fresh normal blood and to each of two other test tubes was added 1 ml of fresh sickle blood. The blood samples were washed with isotonic saline, then centrifuged at 3000 rpm for 5 minutes, and then washed again. 5 ml of saline was then added to the packed cells and mixed with them. To each tube was added 0.5 ml (4 gm in 200 ml solution) of the deoxygenating agent sodium dithionite, and to one of the sickle cell tubes was added 25 μg/ml of the inventive extract. The tubes were then placed in a 55° C. water bath.

The deoxygenation which occurred was indicated by the color changes. The color changes were recorded every 24 minutes and were denoted by 0+, 1+, 2+, and 3+. As the colors changed from red to brown, the numbers increased until finally the cells were a dark brown and there was no more color change (i.e., equilibrium was reached). The results are shown in Table 11.

TABLE 11

| | Color Change | | | | |
|---|---|---|---|---|---|
| | 24 min | 48 min | 72 min | 96 min | 120 min |
| Normal Cell Sodium dithionite | — | — | (1+) | (2+) | (3+) |
| Untreated Sickle Cell Sodium dithionite | (3+) | (3+) | (3+) | (3+) | (3+) |
| Treated Sickle Cell (25 μg/ml) Sodium dithionite | (1+) | (1+) | (2+) | (2+) | (3+) |

EXAMPLE 12

Bioassay 9: The Effect of the Inventive Extract on the Concentration of Free Intracellular Calcium [$Ca^{++}$]

In the sickling state, the red blood cells of sickle cell patients contain more than the normal concentration (3–4 times) of the calcium ions as a result of ATP depletion. Since there are little or no endocytic vesicles for calcium ion storage, most of the calcium ions are bound to membrane proteins, thereby resulting in dehydration and hemochrome formation, with a resulting loss of red blood cell deformability and cell-to-cell adherence. A DMX 1000 TM, a multiparameter cation measuring spectroflurometer, and Fura-2AM, an intracellular $Ca^{++}$ probe, were used to determine the effect of the inventive drug on the concentration of free intracellular calcium ion $[Ca^{++}]_i$ of treated and untreated normal and sickle red blood cells. Changes in free $[Ca^{++}]_i$ were determined by measuring changes in the fluorescence ratio of Fura-2AM at two characteristic excitation wavelengths (340 nm and 380 nm) (Tsien et al., *Cell Calcium*, 6:145–147 (1985)). Determination of free $[Ca^{++}]_i$ in treated and untreated normal red blood cells, sickle red blood cells homozygous for HbS (i.e. HbSS), and sickle red blood cell carriers for HbS (i.e. HbAS was made by incubating the samples for 30 minutes at 37° C., followed by an additional incubation with Fura-2AM for 45 minutes. The results of this study, shown in Table 12, revealed that the extract of the present invention released and prevented the binding of excess calcium ions to the red blood cell membranes, thereby reversing and/or preventing the sickling process.

TABLE 12

| Free $[Ca^{++}]_i$ (nm) Determination | | |
|---|---|---|
| | Treated | Untreated |
| Normal Red Blood Cells | 90 ± 5 | 90 ± 5 |
| HbSS Red Blood Cells | 335 ± 10 | 65 ± 15 |
| HbAS Red Blood Cells | 115 ± 5 | 75 ± 5 |

EXAMPLE 13

Clinical Study

The extract of the present invention was administered in a second clinical study to ten children over a period of three months. During the study, the general condition of the children, their clinical symptoms, hematology, and biochemistry were observed.

To facilitate administration, the inventive extract was admixed with an inert medium into a pharmaceutically acceptable formulation. Pharmaceutical formulation of the extract comprised dissolving the drug in mineral oil at a concentration of 25 mg per 0.175 ml, which is the fill volume of the standard two-part gelatin capsule into which it was then sealed. Mineral oil was chosen as a vehicle since it had been shown to have no biological effects at all at these levels. Depending on the patient, two to four capsules were administered to each patient daily.

Oral administration of the inventive extract gave satisfactory results in general, and in some cases excellent results. The ten children that were evaluated were classified as having Class III sickle cell disease, meaning that they had one or more crises per month, and that their general conditions were not stable. After treatment, a clear improvement was observed in seven of the ten children, including disappearance of crises, increases in weight, and a slight elevation in hemoglobin levels. Consequently, their general condition was well improved. One patient had both sickle cell disease and thalassemia, one patient had HbSC, and another patient suffered from β-thalassemia alone. All three of these patients showed significant progress in all test parameters and especially in the hemoglobin concentration, cholesterol level, and in the number of hospitalizations. One patient, however, had a case of hyperuricemia that persisted for two months, possibly accounting for the recurrence of vasooclusive crises. Two other patients presented one crisis per month; however, more probably than not, these were associated with a malarial/bacterial infection (i.e., pneumonia).

Daily administration of the inventive extract to the ten children resulted in a reduction in the number of crises in 70% of the cases. Further, from a total of 92 crises per year (i.e., 23 per trimester) for the entire group studied, the number of crises was reduced to eight for the trimester studied. And only three of those crises necessitated hospitalization, all for under five days.

The extract of the present invention was shown to have a significant positive effect on β-thalassemia and sickle cell C (i.e. HbSC) patients. The inventive extract stimulated the production of HbF to beneficial levels and decreased significantly the white blood cell count. The biochemical parameters were greatly improved (i.e. all to normal values), and are shown in Table 14.

TABLE 14

Data on average percent increase or decrease (to normal values) of biochemical and hematologic parameters of patients treated with the inventive extract for 12 weeks. (All patients had abnormal values before treatment).

| | Increase | Decrease |
|---|---|---|
| Cholesterol | — | 30% |
| Bilirubin | — | 41.3% |
| Transaminase | | |
| SGOT | — | 56% |
| SGPT | — | 50% |
| Hematoerit | 5.2% | — |
| HbF | 10% | |
| Weight (Kgm) | 0.1% | — |
| WBC | — | 59% |
| Hemolysis | — | 50% |

The one patient in the study having β-thalassemia had suffered five crises, resulting in five hospitalizations, over a twelve-month period prior to the study. 75 mg of the inventive extract was administered to this patient over a three-month period. During this period of treatment, the patient suffered no crises. Further, the patient's biochemical parameters also improved, including an increase in hematocrit and hemoglobin and a decrease in bilirubin levels and liver enzymes, as shown in Table 15.

TABLE 15

Biochemical data on β-thalassemia patient prior to and during treatment with the inventive extract (75 mg/daily)

| Biochemical parameters | Initial level | Levels 1 mon. | Levels 2 mos. | Levels 3 mos. |
|---|---|---|---|---|
| Hct (%) | 20 | 25 | 26 | 27 |
| Hgb (g %) | 6.9 | 7.7 | 8.4 | 8.6 |
| Transaminase | | | | |
| SGOT | 27 | 15 | 17 | 12 |
| SGPT | 22 | 10 | 8 | 8 |
| Bilirubin (total) | 12.4 | 10 | 9 | 9 |

The invention has been described with reference to its preferred embodiments. A person of ordinary skill in the art, having read the above specification, may appreciate modifications that are within the scope and spirit of the invention as described above and claimed below.

What is claimed is:

1. A method for treating hemoglobinopathies, selected from the group consisting of sickle cell anemia and thalassemia, in humans comprising administering a therapeutically effective amount of an extract consisting essentially of linolenic acid derivatives substantially free of porphyrins obtained from an extraction process, said extraction process comprising the steps of:
   a. soaking a plant material in a sufficient amount of base for a time sufficient to dissolve said extract into said base to form a base solution comprising said extract;
   b. filtering said base solution to form a filtrate;
   c. washing said filtrate with a sufficient amount of water to form a washed filtrate;
   d. acidifying said washed filtrate to form an acidic solution;
   e. extracting said acidic solution at least once with an amount of an organic solvent, selected from the group consisting of hexane, 1,1,1-trichloroethane, chloroform, and methylene chloride, sufficient to produce an organic solvent solution;
   f. filtering said organic solvent solution to produce a second filtrate; and
   g. removing said organic solvent from the second filtrate to yield a residue comprising said extract.

2. The method of claim 1, wherein said organic solvent is hexane.

3. The method of claim 1, wherein said plant material is alfalfa.

4. The method of claim 1, wherein said therapeutically effective amount is from about 6.25 mg to about 200 mg.

5. The method of claim 1, wherein in step (e) the said organic solvent is selected from the group consisting of 1,1,1-trichloroethane, chloroform, and methylene chloride, and wherein said extraction process further comprises after the removing step, the steps of:
   a. adding acidified water and a sufficient amount of methanol to the residue to form an aqueous phase;
   b. adding a sufficient amount of hexane to said aqueous phase to form an organic phase;
   c. shaking together said aqueous phase with said organic phase to transfer said extract from said aqueous phase into said organic phase; and
   d. removing by distillation hexane from the shaken organic phase to yield a second residue comprising said extract.

6. The method of claim 5, wherein said organic solvent is 1,1,1-trichloroethane.

* * * * *